(12) United States Patent
Zhuang et al.

(10) Patent No.: US 7,776,613 B2
(45) Date of Patent: Aug. 17, 2010

(54) SUB-DIFFRACTION IMAGE RESOLUTION AND OTHER IMAGING TECHNIQUES

(75) Inventors: Xiaowei Zhuang, Cambridge, MA (US); Wilfred Mark Bates, Somerville, MA (US); Michael J. Rust, Medford, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 386 days.

(21) Appl. No.: 11/605,842

(22) Filed: Nov. 29, 2006

(65) Prior Publication Data

US 2008/0032414 A1 Feb. 7, 2008

Related U.S. Application Data

(60) Provisional application No. 60/836,167, filed on Aug. 7, 2006, provisional application No. 60/836,170, filed on Aug. 8, 2006.

(51) Int. Cl.
*G01N 21/76* (2006.01)
(52) U.S. Cl. .................. 436/172; 436/164; 436/171
(58) Field of Classification Search .................. None
See application file for complete search history.

(56) References Cited

U.S. PATENT DOCUMENTS 6,008,373 A 12/1999 Waggoner et al.

(Continued)

FOREIGN PATENT DOCUMENTS

WO WO 2006/127692 A2 11/2006

OTHER PUBLICATIONS

Bates et al. "Short-Range Spectroscopic Ruler Based on a Single-Molecule Optical Switch". 2005. Physical Review Letters. vol. 94, pp. 108101-1 to 108101-4.*

(Continued)

*Primary Examiner*—Yelena G Gakh
*Assistant Examiner*—David Weisz
(74) *Attorney, Agent, or Firm*—Wolf, Greenfield & Sacks, P.C.

(57) ABSTRACT

The present invention generally relates to sub-diffraction image resolution and other imaging techniques. In one aspect, the invention is directed to determining and/or imaging light from two or more entities separated by a distance less than the diffraction limit of the incident light. For example, the entities may be separated by a distance of less than about 1000 nm, or less than about 300 nm for visible light. In one set of embodiments, the entities may be selectively activatable, i.e., one entity can be activated to produce light, without activating other entities. A first entity may be activated and determined (e.g., by determining light emitted by the entity), then a second entity may be activated and determined. The emitted light may be used to determine the positions of the first and second entities, for example, using Gaussian fitting or other mathematical techniques, and in some cases, with sub-diffraction resolution. The methods may thus be used, for example, to determine the locations of two or more entities immobilized relative to a common entity, for example, a surface, or a biological entity such as DNA or a protein. The entities may also be determined with respect to time, for example, to determine a time-varying reaction. Other aspects of the invention relate to systems for sub-diffraction image resolution, computer programs and techniques for sub-diffraction image resolution, methods for promoting sub-diffraction image resolution, methods for producing photoswitchable entities, and the like.

18 Claims, 10 Drawing Sheets

U.S. PATENT DOCUMENTS

| | | | |
|---|---|---|---|
| 7,535,012 | B2 | 5/2009 | Betzig et al. |
| 7,626,694 | B2 | 12/2009 | Betzig et al. |
| 7,626,695 | B2 | 12/2009 | Betzig et al. |
| 7,626,703 | B2 | 12/2009 | Betzig et al. |
| 2002/0064789 | A1* | 5/2002 | Weiss et al. .................... 435/6 |
| 2003/0087282 | A1 | 5/2003 | Oshida et al. |
| 2006/0038993 | A1 | 2/2006 | Hell |

OTHER PUBLICATIONS

Dailey et al. "Confocal Microscopy of living Cells." 2006. Handbook of Biological Confocal Microscopy, 3rd. Ed. Chapter 19, pp. 381-403.*

Amato, I., "Squint Busters: Tool builders are pushing optical microscope vision to single-molecule sharpness," *Chemical & Engineering News*, Sep. 4, 2006, pp. 49-52.

Betzig, E., et al., "Imaging Intracellular Fluorescent Proteins at Nanometer Resolution," *ScienceExpress*, Aug. 10, 2006, pp. 1-9 (2006).

Betzig, E., et al., "Imaging Intracellular Fluorescent Proteins at Nanometer Resolution (Supporting Online Material)," http:www.sciencemag.org/cgi/content/full/1127344/DC1, pp. 1-30 (2006).

Wang, W., et al., "Label-free detection of small-molecule-protein interactions by using nanowire nanosensors," *Proc. Natl. Acad. Sci. USA*, vol. 102, No. 9, pp. 3208-3212 (2005).

"Frontiers in live cell imaging/NIGMS and the Cell Migration Consortium (Movie)," National Institute of General Medical Sciences, National Institute of General Medical Sciences, Apr. 20, 2006, http://videocast.nih.gov/launch.asp?13187.

Betzig, E. "Proposed method for molecular optical imaging," *Optics Letters*, vol. 20, No. 3, Feb. 1, 1995, pp. 237-239.

Bates, Mark et al., "Super-resolution microscopy by nanoscale localization of photo-switchable fluorescent probes" Current Opinion in Chemical Biology 2008, 12 505-514.

Friedman et al. "Viewing dynamic assembly of molecular complexes by multi-wavelength single-molecule fluorescence" *Biophysical J*, vol. 91:1023-1031 (Aug. 2006).

Habuchi et al. "Reversible single-molecule photoswitching in the GFP-like fluorescent protein Dronpa" PNAS vol. 102, No. 27: 9511-9516 (Jul. 5, 2005).

Hess, Samuel T., et al. "Ultra-High Resolution Imaging by Fluorescence Photoactivation Localization Microscopy" Biophysical Journal, vol. 91, Dec. 2006 4258-4272.

Hofmann et al. "Breaking the diffraction barrier in fluorescence microscopy at low light intensities by using reversibly photoswitchable proteins" PNAS vol. 12, No. 49: 17565-17569 (Dec. 6, 2005).

Huang, Bo et al. "Three-Dimensional Super-Resolution Imaging by Stochastic Optical Reconstruction Microscopy" Science, Feb. 8, 2008, vol. 319, pp. 810-813.

Kao, H. Pin et al. "Tracking of Single Fluorescent Particles in Three Dimensions: Use of Cylindrical Optics of Encode Particle Position" Biophysical Journal, vol. 57, Sep. 1994, pp. 1291-1300.

Juette, Manuel F. et al. "Three-Dimensional sub-100 nm resolution fluorescence microscopy of thick samples" Nature Methods, vol. 5, No. 6, Jun. 2008, 527-529.

Lecoste, Thilo D. et al. "Ultrahigh-resolution multicolor colocalization of single fluorescent probes" PNAS, Aug. 15, 2000, vol. 97, No. 17, pp. 9461-9466.

Prabhat, Prashant et al. "Simultaneous imaging of several focal planes in fluorescence microscopy for the study of cellular dynamics in 3D" Proc. of SPIE vol. 6090 (2006).

Rust et al. Sub-diffraction-limit imaging by stochastic optical reconstruction microscopy (STORM) *Nature Methods* p. 1-3 (Aug. 9, 2006).

Speidel, Michael et al. "Three-dimensional tracking of fluorescent nanoparticles with subnanometer precision by use of off-focus imaging" Optics Letters, Jan. 15, 2003, vol. 28, No. 2, pp. 69-71.

Toprak, Erdal et al. "Three-Dimensional Particle Tracking via Bifocal Imaging"Nano Letters 2007 vol. 7, No. 7, pp. 2043-2045.

Van Oijen, A.M, et al. "3-Dimensional super-resolution by spectrally selective imaging" Chemical Physics Letters 292 (1998) 183-187.

International Search Report from International Patent Application PCT/US07/017618 dated Feb. 10, 2009.

Hell, S.W. et al. "Breaking the diffraction resolution limit by stimulated emission: stimulated-emission-depletion fluorescence microscopy," J Opt Lett (1994) 19:780.

Huang, B. et al. "Whole-cell 3D STORM reveals interactions between cellular structures with nanometer-scale resolution," Nat Meth (2008) 5:1047.

Pavani, S. et al. "Three Dimensional, single-molecule fluorescence imaging beyond the diffraction limit by using a double-helix point spread function," PNAS (2009) 106, 2995.

Schmidt, R. et al. "Mitochondrial Cristae Revealed with Focused Light," Nano Lett (2009) 9:2508.

Schmidt, R. et al. "Spherical nanosized focal spot unravels the interior of cells," Nat Meth (2008) 5:539.

Shtengel, G. et al. "Interferometric fluorescent super-resolution microscopy resolves 3D cellular ultrastructure," PNAS (2009) 106, 3125.

Vaziri, A. et al. "Multilayer three-dimensional super resolution imaging of thick biological samples," PNAS (2008) 105, 20221.

Office Action dated Jun. 12, 2009 in U.S. Appl. No. 12/012,524.

Office Action dated Jan. 15, 2010 in U.S. Appl. No. 12/012,524.

Office Communication dated Jun. 15, 2009 in EP 07872605.6.

Ando, et al., "Regulated Fast Nucleocytoplasmic Shuttling Observed by Reversible Protein Highlighting," *Science*, 306, 1370, 2004.

* cited by examiner

Cy3

Cy5

SUB-DIFFRACTION IMAGE RESOLUTION AND OTHER IMAGING TECHNIQUES

RELATED APPLICATIONS

This application claims priority to all of the following according to the following recitation of priority relationships. This application claims the benefit of U.S. Provisional Patent Application Ser. No. 60/836,167, filed Aug. 7, 2006, entitled "Sub-Diffraction Image Resolution"; and the benefit of U.S. Provisional Patent Application Ser. No. 60/836,170, filed Aug. 8, 2006, entitled "Sub-Diffraction Image Resolution." Each of the above is incorporated herein by reference.

GOVERNMENT FUNDING

This invention was made with U.S. Government support under GM068518 awarded by the National Institutes of Health and under N66001-04-1-8903 awarded by U.S. Navy SPAWAR/SD. The U.S. Government has certain rights in the invention.

FIELD OF INVENTION

The present invention generally relates to sub-diffraction image resolution and other imaging techniques.

BACKGROUND

Fluorescence microscopy is widely used in molecular and cell biology and other applications for non-invasive, time-resolved imaging. Despite these advantages, standard fluorescence microscopy is not useful for ultra-structural imaging, due to a resolution limit set by the diffraction of light. Several approaches have been employed to try to pass this diffraction limit, including near-field scanning optical microscopy (NSOM), multi-photon fluorescence, stimulated emission depletion (STED), and saturated structured-illumination microscopy (SSIM), but each has certain unsatisfactory limitations. Electron microscopy is often used for high resolution imaging of biological samples, but electron microscopy uses electrons, rather than light, and is difficult to use with biological samples due to its preparation requirements. Accordingly, new techniques are needed to harness the benefits of fluorescence microscopy for ultra-resolution imaging of biological and other samples.

SUMMARY OF THE INVENTION

The present invention generally relates to sub-diffraction image resolution and other imaging techniques. The subject matter of the present invention involves, in some cases, inter-related products, alternative solutions to a particular problem, and/or a plurality of different uses of one or more systems and/or articles.

The invention is a method, in one aspect. In one set of embodiments, the method includes acts of providing a first entity and a second entity separated by a distance of less than about 1000 nm, determining light emitted by the first entity, determining light emitted by the second entity, and determining the positions of the first entity and the second entity by using the light emitted by the first entity and the light emitted by the second entity. In another set of embodiments, the method includes acts of providing a first entity and a second entity separated by a distance of less than about 1000 nm, activating the first entity but not the second entity, determining light emitted by the first entity, activating the second entity, determining light emitted by the second entity, and determining the positions of the first entity and the second entity by using the light emitted by the first entity and the light emitted by the second entity.

The method, according to yet another set of embodiments, includes acts of providing a plurality of entities able to emit light, at least some of which are separated by a distance of less than about 1000 nm, activating a fraction of the plurality of entities to emit light, determining the emitted light, deactivating the activated fraction of the plurality of entities, and repeating the acts of activating and deactivating the plurality of entities to determine the positions of the plurality of entities.

In another set of embodiments, the method includes acts of providing a first entity and a second entity separated by a distance of separation, determining light emitted by the first entity, the light emitted by the first entity having a wavelength greater than the distance of separation, determining light emitted by the second entity, and determining the positions of the first entity and the second entity by using the light emitted by the first entity and the light emitted by the second entity. The method, in yet another set of embodiments, includes acts of providing a first entity and a second entity separated by a distance of separation, activating the first entity but not the second entity, determining light emitted by the first entity, the light emitted by the first entity having a wavelength greater than the distance of separation, activating the second entity, determining light emitted by the second entity, and determining the positions of the first entity and the second entity by using the light emitted by the first entity and the light emitted by the second entity.

In one set of embodiments, the method includes acts of providing a plurality of entities able to emit light, at least some of which are separated by a distance of separation less than the wavelength of the emitted light, activating a fraction of the plurality of entities to emit light, determining the emitted light, deactivating the activated fraction of the plurality of entities, and repeating the acts of activating and deactivating the plurality of entities to determine the positions of the plurality of entities.

The method, in another set of embodiments, includes acts of providing a first entity and a second entity separated by a distance of less than about 1000 nm where the first entity and the second entity each are immobilized relative to a common entity, determining the positions of the first entity and the second entity at a first point of time, determining the positions of the first entity and the second entity at a second point of time, and determining movement of the common entity using the positions of the first and second entities at the first and second points of time. In yet another set of embodiments, the method includes acts of providing a first entity and a second entity separated by a distance of separation where the first entity and the second entity are each immobilized relative to a common entity, determining the positions of the first entity and the second entity at a first point of time using light emitted by the first entity and light emitted by the second entity where the light emitted by the first entity has a wavelength greater than the distance of separation, determining the positions of the first entity and the second entity at a second point of time, and determining movement of the common entity using the positions of the first and second entities at the first and second points of time.

In still another set of embodiments, the method includes acts of identifying, within a series of images in time, one or more light-emission regions, each generated by a single entity; for each light-emission region, identifying the center of the light-emission region; and for each light-emission region, reconstructing the position of the single entity generating the light-emission region at a resolution greater than the wavelength of the light emitted by the single entity.

In another aspect, the invention is directed to an article including a translation stage for a microscope having a drift of less than about 100 nm/min.

Still another aspect of the invention is directed to an imaging composition. The composition, according to one set of embodiments, includes a light-emitting entity, capable of being reversibly switched between a first state able to emit light at a first, emission wavelength and a second state that does not substantially emit light at the first wavelength. In one embodiment, the light-emitting entity comprises a first portion that is capable of emitting light at the first wavelength, and a second portion that activates the first portion upon exposure to an external stimulus, thereby causing the first portion to emit light at the first wavelength.

In another aspect, the present invention is directed to a system for performing one or more of the embodiments described herein. In another aspect, the present invention is directed to computer programs and techniques for performing one or more of the embodiments described herein. For example, one embodiment of the invention is directed to a machine-readable medium comprising a program, embodied in the medium, for causing a machine to perform a method comprising acts of identifying, within a series of images in time, one or more light-emission regions, each generated by a single entity; for each light-emission region, identifying the center of the light-emission region; and for each light-emission region, reconstructing the position of the single entity generating the light-emission region at a resolution greater than the wavelength of the light emitted by the single entity.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
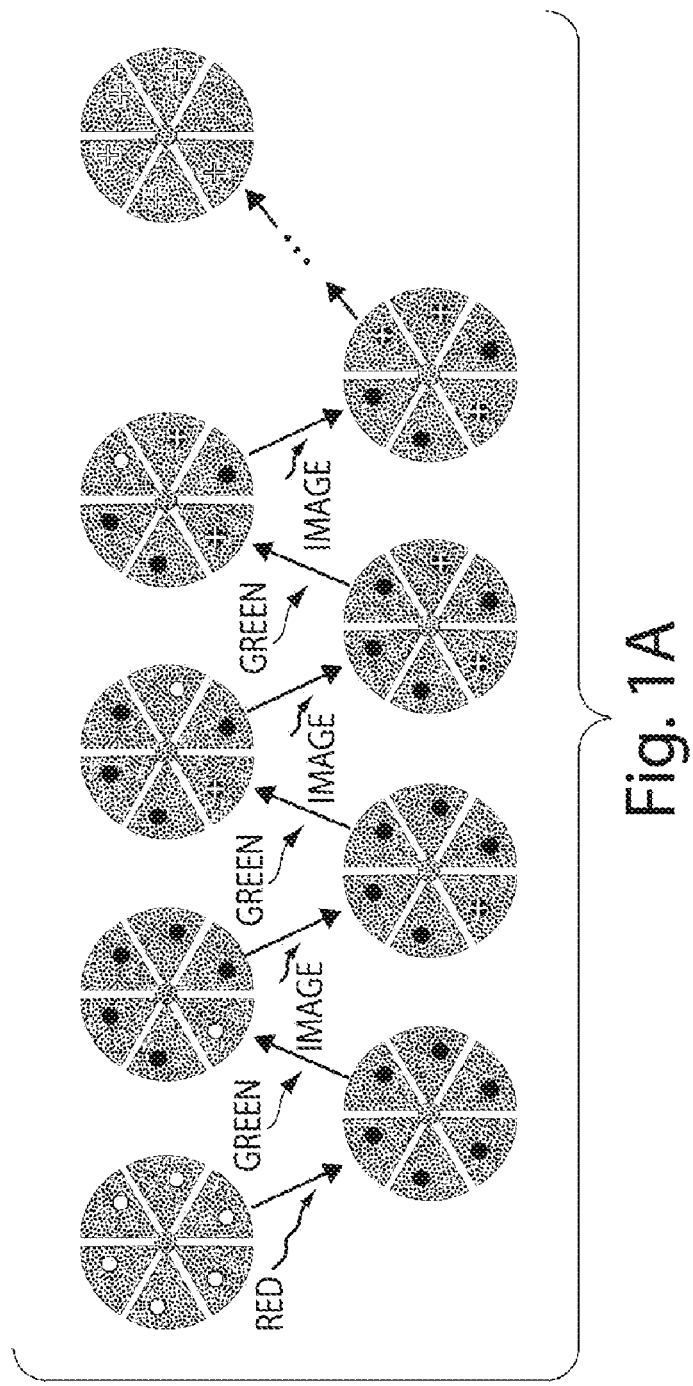
FIGS. 1a-1b illustrate sub-diffraction resolution of an image according to one embodiment of the invention.

The present invention generally relates to sub-diffraction image resolution and other imaging techniques. In one aspect, the invention is directed to determining and/or imaging light from two or more entities separated by a distance less than the diffraction limit of the incident light. For example, the entities may be separated by a distance of less than about 1000 nm, or less than about 300 nm for visible light. In one set of embodiments, the entities may be selectively activatable, i.e., one entity can be activated to produce light, without activating other entities. A first entity may be activated and determined (e.g., by determining light emitted by the entity), then a second entity may be activated and determined. The emitted light may be used to determine the positions of the first and second entities, for example, using Gaussian fitting or other mathematical techniques, and in some cases, with sub-diffraction resolution. The methods may thus be used, for example, to determine the locations of two or more entities immobilized relative to (directly or indirectly, e.g., via a linker) a common entity, for example, a surface, or a biological entity such as DNA or a protein. The entities may also be determined with respect to time, for example, to determine a time-varying reaction. Other aspects of the invention relate to systems for sub-diffraction image resolution, computer programs and techniques for sub-diffraction image resolution, methods for promoting sub-diffraction image resolution, methods for producing photoswitchable entities, and the like.

In various aspects of the invention, any entity able to emit light may be used. The entity may be a single molecule in some cases. Non-limiting examples of emissive entities include fluorescent entities (fluorophores) or phosphorescent entities, for example, Cy2, Cy3, Cy5, metal nanoparticles, semiconductor nanoparticles or "quantum dots," or fluorescent proteins such as GFP (Green Fluorescent Protein). Other light-emissive entities are readily known to those of ordinary skill in the art. As used herein, the term "light" generally refers to electromagnetic radiation, having any suitable wavelength (or equivalently, frequency). For instance, in some embodiments, the light may include wavelengths in the optical or visual range (for example, having a wavelength of between about 400 nm and about 700 nm, i.e., "visible light"), infrared wavelengths (for example, having a wavelength of between about 300 micrometers and 700 nm), ultraviolet wavelengths (for example, having a wavelength of between about 400 nm and about 10 nm), or the like. In certain cases, as discussed in detail below, more than one entity may be used, i.e., entities that are chemically different or distinct, for example, structurally. However, in other cases, the entities may be chemically identical.

In one set of embodiments, the entity is "switchable," i.e., the entity can be switched between two or more states, at least one of which emits light having a desired wavelength. In the other state(s), the entity may emit no light, or emit light at a different wavelength. For instance, an entity may be "activated" to a first state able to produce light having a desired wavelength, and "deactivated" to a second state. As a non-limiting example, Cy5, can be switched between a fluorescent and a dark state in a controlled and reversible manner by light of different wavelengths, i.e., 633 nm red light can switch or deactivate Cy5 to a stable dark state, while 532 nm green light can switch or activate the Cy5 back to the fluorescent state. In some cases, the entity can be reversibly switched between the two or more states, e.g., upon exposure to the proper stimuli. For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one embodiment, incident light of a suitable wavelength may be used to activate the entity to emit light. The light may be monochromatic (e.g., produced using a laser) or polychromatic. In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc. Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a much reduced intensity) when exposed to the excitation wavelength.

In one set of embodiments, as discussed, a switchable entity may be switched upon exposure to light. In some cases, the light used to activate the switchable entity may come from an external source (e.g., a light source such as a fluorescent light source, another light-emitting entity proximate the switchable entity, etc.). The second, light emitting entity, in some cases, may be a fluorescent entity, and in certain embodiments, the second, light-emitting entity may itself also be a switchable entity.

Figure 7A:
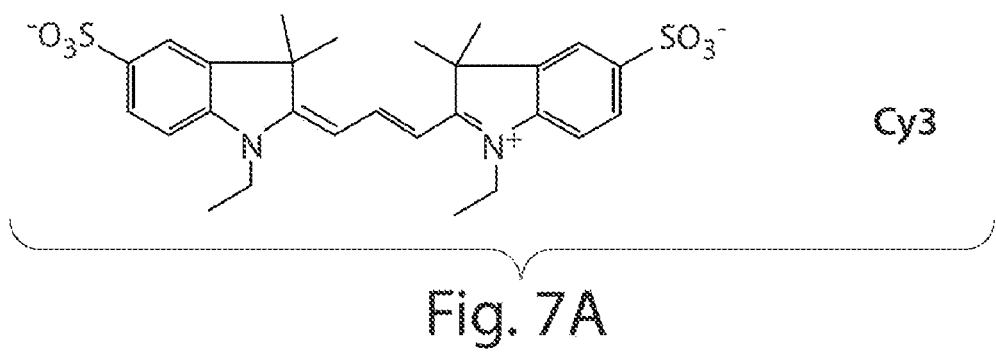
FIGS. 7A-7C respectively illustrate the structures of Cy3, Cy5, and an example of a linked Cy3-Cy5 moiety.
Figure 7B:
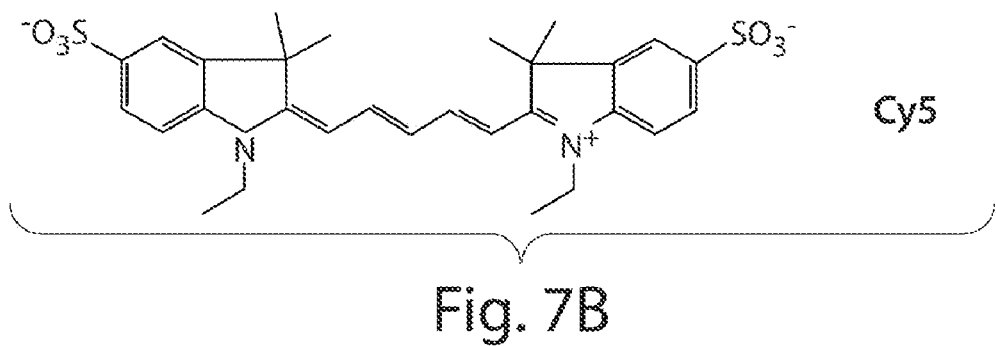
Figure 7C:
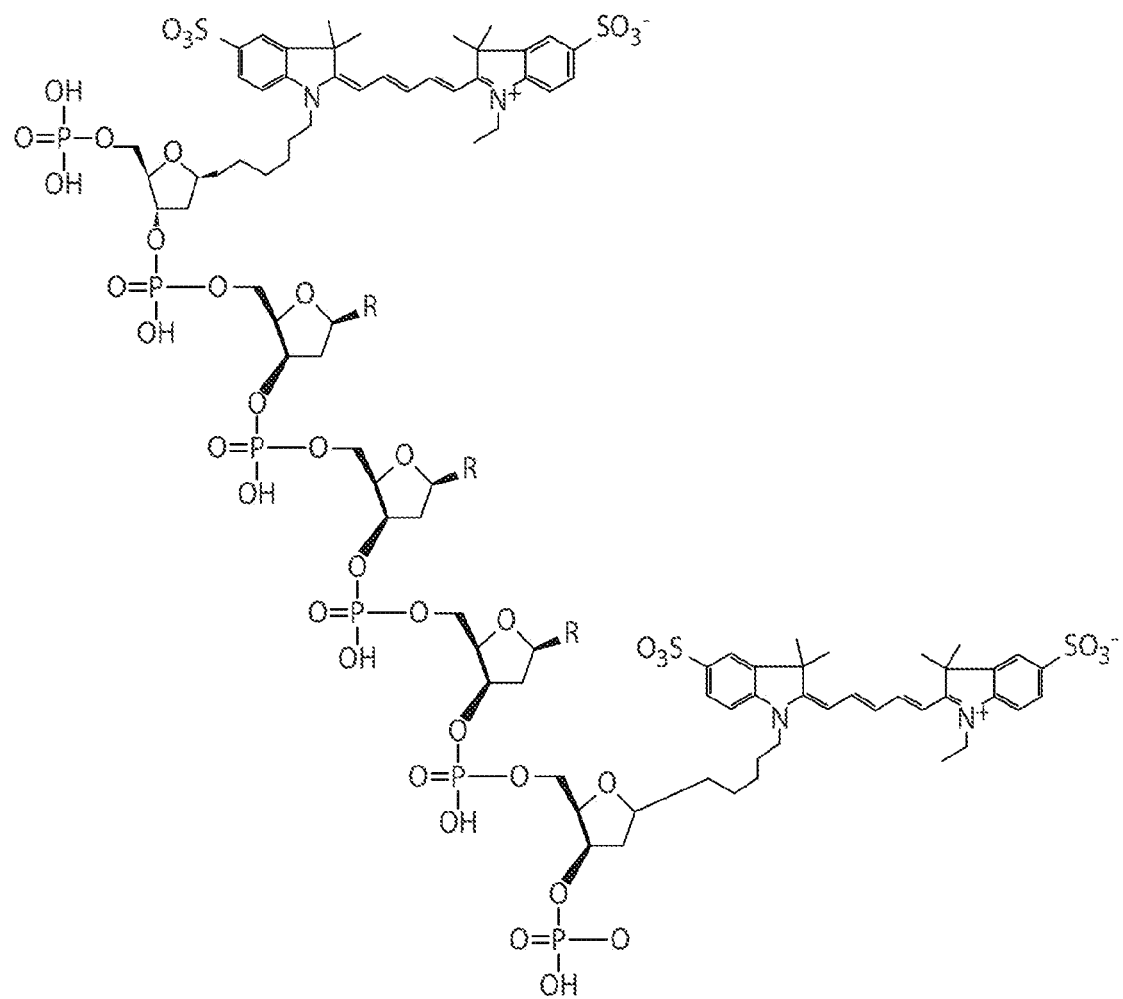

In some embodiments, the switchable entity includes a first, light-emitting portion (e.g., a fluorophore), and a second portion that activates or "switches" the first portion. For example, upon exposure to light, the second portion of the switchable entity may activate the first portion, causing the first portion to emit light. Examples of activator portions include, but are not limited to, Alexa 488 (Molecular Probes), Cy2, Cy3, Cy3.5, or Cy5. Examples of light-emitting portions include, but are not limited to, Cy5, Cy5.5, or Cy7. These may linked together, e.g., covalently, for example, directly, or through a linker, e.g., forming compounds such as, but not limited to, Cy5-Alexa 488, Cy5-Cy2, Cy5-Cy3, Cy5-Cy3.5, Cy5.5-Alexa 488, Cy5.5-Cy2, Cy5.5-Cy3, Cy5.5-Cy3.5, Cy7-Alexa 488, Cy7-Cy2, Cy7-Cy3, Cy7-Cy3.5, or Cy7-Cy5. The structures of Cy3 and Cy5 are shown in FIG. 7, with a non-limiting example of a linked version of Cy3-Cy5 shown in FIG. 7C; those of ordinary skill in the art will be aware of the structures of these and other compounds, many of which are available commercially. For example, Cy3 and Cy5 may be obtained from Amersham Bioscience. The portions may be linked via a covalent bond, or by a linker, such as those described in detail below.

In certain cases, the light-emitting portion and the activator portions, when isolated from each other, may each be fluorophores, i.e., entities that can emit light of a certain, emission wavelength when exposed to a stimulus, for example, an excitation wavelength. However, when a switchable entity is formed that comprises the first fluorophore and the second fluorophore, the first fluorophore forms a first, light-emitting portion and the second fluorophore forms an activator portion that switches that activates or "switches" the first portion in response to a stimulus, instead of emitting light. Whether a pair of light-emitting portion and activator portion produces a suitable switchable entity can be tested by methods known to those of ordinary skills in the art. For example, light of various wavelength can be used to stimulate the pair and emission light from the light-emitting portion can be measured to determined wither the pair makes a suitable switch.

As a non-limiting example, Cy3 and Cy5 may be linked together to form such an entity. Such a procedure is described in more detail in the Examples, below. In this example, Cy3 is an activator portion that is able to activate Cy5, the light-emission portion. Thus, light at or near the absorption maximum (e.g., near 532 nm light for Cy3) of the activation or second portion of the entity may cause that portion to activate the first, light-emitting portion, thereby causing the first portion to emit light (e.g., near 633 nm for Cy5). As previously described, the first, light-emitting portion can subsequently be deactivated by any suitable technique (e.g., by directing 633 nm red light to the Cy5 portion of the molecule).

Accordingly, in one embodiment of the invention, a light-emitting switchable entity is provided, comprising a first, light emitting portion and a second, activation portion. The entity has a maximum emission wavelength determined by the first, light emitting portion and a maximum activation wavelength determined by the second, activation portion. Notably, the two wavelengths are not controlled by the same molecular entity, and are effectively decoupled. Further, multiple types of switchable entities within a sample may be independently determined, e.g., by exposing the sample to a first, excitation energy or wavelength, and determining emission of a second, emission wavelength from the sample, while ignoring other emission wavelengths. Thus, two switchable entities having the same activator portions but different light-emission portions can be activated by the same wavelength light applied to the sample, but emit at different wavelengths due to different light-emission portions and can be easily distinguished, even at separation distances of less than sub-diffraction resolutions. This can effectively yield two colors in the image. Similarly, two switchable entities having the same light-emission portions but different activator portions can be activated by different wavelength light applied to the sample, due to the different activator portions, and the light-emission portions may emit at same wavelengths and can thus be distinguished, even at separation distances of less than sub-diffraction resolutions. This also can effectively yield two colors in the image. When these methods are combined, four (or more) color images can be readily produced. Using this principle, multi-color imaging can be scaled up to 6 colors, 9 colors, etc., depending on the switchable and/or activator entities. This multi-color imaging principle may also be used with the imaging methods described herein to yield sub-diffraction resolutions.

In contrast, fluorescent dyes commonly used by those of ordinary skill in the art (e.g., isolated Cy5) inherently have a maximum excitation wavelength and a maximum emission wavelength that are each determined by the nature and structure of the fluorescent dye, and cannot be independently controlled. Thus, the invention, in another set of embodiments, provides a range of switchable entities where the first, light emitting portion and the second, activation portion are each independently selected. Accordingly, in some embodiments, a larger set of colors is provided, e.g., with respect to conventional imaging methods.

Any suitable method may be used to link the first, light-emitting portion and the second, activation portion. In some cases, the link is chosen such that the distance between the first and second portions is sufficiently close to allow the activator portion to activate the light-emitting portion as desired, e.g., whenever the light-emitting portion has been deactivated in some fashion. Typically, the portions will be separated by distances on the order of 100 nm or less, for example, less than about 50 nm, less than about 20 nm, less than about 10 nm, less than about 5 nm, less than about 2 nm, less than about 1 nm, etc. Examples of common entities or linkers that can be used include, but are not limited to, DNA, RNA, PNA, LNA, polypeptides, carbon chains (e.g., alkanes or alkeries), polymer units, or the like.

In one set of embodiments, the switchable entity can be immobilized, e.g., covalently, with respect to a binding partner, i.e., a molecule that can undergo binding with a particular analyte. Binding partners include specific, semi-specific, and non-specific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, but are not limited to, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or van der Waals interactions, etc. By immobilizing a switchable entity with respect to the binding partner of a target molecule or structure (e.g., DNA within a cell), the switchable entity can be used for various determination or imaging purposes. For example, a switchable entity having an amine-reactive group may be reacted with a binding partner comprising amines, for example, antibodies, proteins or enzymes. A non-limiting example of the immobilization of a switchable entity to an antibody is discussed in the Examples, below.

In some embodiments, more than one switchable entity may be used, and the entities may be the same or different. In some cases, the light emitted by a first entity and the light emitted by a second entity have the same wavelength. The entities may be activated at different times and the light from each entity may be determined separately. This allow the location of the two entities to be determined separately and, in some cases, the two entities may be spatially resolved, as discussed in detail below, even at distances of separation that are less than the light emitted by the entities or below the diffraction limit of the emitted light (i.e., "sub-diffraction" resolutions). In certain instances, the light emitted by a first entity and the light emitted by a second entity have different wavelengths (for example, if the first entity and the second entity are chemically different, and/or are located in different environments). The entities may be spatially resolved even at distances of separation that are less than the light emitted by the entities or below the diffraction limit of the emitted light.

Two or more of the switchable entities may be immobilized relative to a common entity in some aspects of the invention. The common entity may be any nonbiological entity or biological entity, for example, a cell, a substrate, a surface, a polymer, or a biological molecule such as a nucleic acid or a protein. As an example, two or more entities may be immobilized relative to a DNA strand or other nucleic acid strand (e.g., using antibodies, substantially complementary oligonucleotides labeled with one or more entities, chemical reactions or other techniques known to those of ordinary skill in the art), and their locations along the strand detected. In some cases, the number of base pairs (bp) separating the entities along the nucleic acid strand may be determined.

In some cases, the entities may be independently switchable, i.e., the first entity may be activated to emit light without activating a second entity. For example, if the entities are different, the methods of activating each of the first and second entities may be different (e.g., the entities may each be activated using incident light of different wavelengths). As another non-limiting example, incident light having a sufficiently weak intensity may be applied to the first and second entities such that only a subset or fraction of the entities within the incident light are activated, i.e., on a stochastic or random basis. The amount of activation may be any suitable fraction, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the entities may be activated, depending on the application. Specific intensities for activation can be determined by those of ordinary skill in the art using no more than routine skill. By appropriately choosing the intensity of the incident light, the first entity may be activated without activating the second entity.

The second entity may be activated to emit light, and optionally, the first entity may be deactivated prior to activating the second entity. The second entity may be activated by any suitable technique, as previously described, for instance, by application of suitable incident light.

The two or more entities may be resolved, even at distances of separation that are less than the wavelength of the light emitted by the entities or below the diffraction limit of the emitted light, according to another aspect of the invention. The resolution of the entities may be, for instance, on the order of 1 micrometer (1000 nm) or less, as described herein. For example, if the emitted light is visible light, the resolution may be less than about 700 nm. In some cases, two (or more) entities may be resolved even if separated by a distance of less than about 500 nm, less than about 300 nm, less than about 200 nm, less than about 100 nm, less than about 80 nm, less than about 60 nm, or less than about 40 nm. In some cases, two or more entities separated by a distance of at least about 20 nm or less than 10 nm can be resolved using embodiments of the present invention.

Light emitted by each of the switchable entities may be determined, e.g., as an image or matrix. For example, the first entity may be activated and the light emitted by the first entity determined, and the second entity may be activated (with or without deactivating the first entity) and light emitted by the second entity may be determined. The light emitted by each of the plurality of entities may be at the same or different wavelengths. Any suitable method may be used to determine the emitted light. For instance, a camera, a photodiode, or a spectrometer may be used; those of ordinary skill in the art will know of other suitable techniques. Additional non-limiting example of a suitable technique for determining light produced by the entities is discussed in the Examples, below. In some cases, multiple images (or other determinations) may be used, for example, to improve resolution and/or to reduce noise. For instance, repeatedly activating and deactivating the plurality of entities and determining the light emitted by each of the entities may be used to facilitate determination the positions of the plurality of entities. Thus, for example, at least 2, at least 5, at least 10, at least 20, at least 25, at least 50, at least 75, at least 100, etc. images may be determined, depending on the application.

In some aspects, the light may be processed to determine the spatial positions of the two or more entities. In some cases, the positions of one or more entities, distributed within an image, may each be individually determined. In one set of embodiments, the emitted light may be processed, using Gaussian fitting or other suitable techniques, to localize the position of each of the emissive entities. Details of one suitable Gaussian fit technique are described in the Examples, below; those of ordinary skill in the art will be able to identify other suitable image-processing techniques with the benefit of the present disclosure.

Another example of an image-processing technique follows, in accordance with another embodiment of the invention. Starting with a series of images of a sample (e.g., a movie), each light-emission peak (e.g., through fluorescence, phosphorescence, etc.) is identified, and the times which the peak is present are determined. For example, a peak may be present with approximately the same intensity in a series of images with respect to time. Peaks which are sporadic, non-elliptical, moving, discontinuously present, etc. are discarded, thus leaving peaks present for a continuous period of time. By determining the center position of the peak, for example, using least-squares fitting to a 2-dimensional Gaussian function of the peak intensities, the location of the source of the peak (e.g., any entity or entities able to emit light, as discussed herein) can be determined. This process may be repeated as necessary for any or all of the peaks within the sample.

Other image-processing techniques may also be used to facilitate determination of the entities, for example, drift correction or noise filters may be used. Generally, in drift correction, for example, a fixed point is identified (for instance, as a fiduciary marker, e.g., a fluorescent particle may be immobilized to a substrate), and movements of the fixed point (i.e., due to mechanical drift) are used to correct the determined positions of the switchable entities. In some embodiments, the drift may be less than about 1000 nm/min, less than about 500 nm/min, less than about 300 nm/min, less than about 100 nm/min, less than about 50 nm/min, less than about 30 nm/min, less than about 20 nm/min, less than about 10 nm/min, or less than 5 nm/min. Such drift may be achieved, for example, in a microscope having a translation stage mounted for x-y positioning of the sample slide with respect to the microscope objective. The slide may be immobilized with respect to the translation stage using a suitable restraining mechanism, for example, spring loaded clips. In addition, a buffer layer may be mounted between the stage and the microscope slide. The buffer layer may further restrain drift of the slide with respect to the translation stage, for example, by preventing slippage of the slide in some fashion. The buffer layer, in one embodiment, is a rubber or polymeric film, for instance, a silicone rubber film. Accordingly, one embodiment of the invention is directed to a device, comprising a translation stage, a restraining mechanism (e.g., a spring loaded clip) attached to the translation stage able to immobilize a slide, and optionally, a buffer layer (e.g., a silicone rubber film) positioned such that a slide restrained by the restraining mechanism contacts the buffer layer.

Multiple locations on a sample may each be analyzed to determine the entities within those locations. For example, a sample may contain a plurality of various entities, some of which are at distances of separation that are less than the wavelength of the light emitted by the entities or below the diffraction limit of the emitted light. Different locations within the sample may be determined (e.g., as different pixels within an image), and each of those locations independently analyzed to determine the entity or entities present within those locations. In some cases, the entities within each location may be determined to resolutions that are less than the wavelength of the light emitted by the entities or below the diffraction limit of the emitted light, as previously discussed.

As noted, in some embodiments, more than one type of switchable entity may be used in a sample, and the positions of each of the entities may be independently determined, in some cases, at sub-diffraction resolutions. For instance, by repeatedly activating and deactivating particular switchable entities in a sample, the positions of a plurality of switchable entities may be determined, in some cases, to resolutions that are less than the wavelength of the light emitted by the entities or below the diffraction limit of the emitted light.

As a non-limiting example, a sample may contain two types of light emitting portions (e.g., Cy5 and Cy5.5) and two types of activation portions (e.g., Cy3 and Cy2), for a total of four (2×2) types of switchable entities: Cy5-Cy3, Cy5-Cy2, Cy5.5-Cy3, and Cy5.5-Cy2. The Cy3-containing entities can be activated by applying light at a suitable wavelength without activating the Cy2-containing entities (since different activation wavelengths are required) while light emitted by the Cy5-containing molecules can be distinguished from light emitted by the Cy5.5-containing molecules (which emits light at a different wavelength). Thus, only the Cy5-Cy3 entities will be determined, while the other entities are either not activated, or are activated but the light emitted by those entities is not used. By using the above-described techniques, the positions of the Cy5-Cy3 entities may be determined within a sample, even to resolutions that are less than the wavelength of the light emitted by Cy5. Additionally, by repeating this procedure using suitable activation and emission wavelengths, the positions of the other entities may also be determined, e.g., to sub-diffraction resolutions. Accordingly, multi-color imaging (e.g., 4 colors, 6 colors, 8 colors, 9 colors, 10 colors, 12 colors, etc.) with sub-diffraction resolutions may be realized.

In some embodiments of the invention, the entities may be also be resolved as a function of time. For example, two or more entities may be observed at various time points to determine a time-varying process, for example, a chemical reaction, cell behavior, binding of a protein or enzyme, etc. See the Examples, below, for an example of the determination of a time-varying process. Thus, in one embodiment, the positions of two or more entities may be determined at a first point of time (e.g., as described herein), and at any number of subsequent points of time. As a specific example, if two or more entities are immobilized relative to a common entity, the common entity may then be determined as a function of time, for example, time-varying processes such as movement of the common entity, reactions involving the common entity, or the like. The time-resolved imaging may be facilitated in some cases since a switchable entity can be switched for multiple cycles, each cycle give one data point of the position of the entity.

Another aspect of the invention is directed to a computer-implemented method. For instance, a computer and/or an automated system may be provided that is able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. The processing steps may also be recorded onto a machine-readable medium in some cases.

Still another aspect of the invention is generally directed to a system able to perform one or more of the embodiments described herein. For example, the system may include a microscope, a device for activating and/or switching the entities to produce light having a desired wavelength (e.g., a laser or other light source), a device for determining the light emitted by the entities (e.g., a camera), and a computer for determining the spatial positions of the two or more entities.

In some embodiments, a microscope may be configured so to collect light emitted by the switchable entities while minimizing light from other sources of fluorescence (e.g., "background noise"). In certain cases, a total-internal-reflection geometry is used for sample excitation. In some embodiments, a thin layer or plane of the sample is exposed to excitation light, which may reduce excitation of fluorescence outside of the sample plane. A high numerical aperture lens may be used to gather the light emitted by the sample. The light may be processed, for example, using filters to remove excitation light, resulting in the collection of emission light from the sample. In some cases, the magnification factor at which the image is collected can be optimized, for example, when the edge length of each pixel of the image corresponds to the length of a standard deviation of a diffraction limited spot in the image.

In some cases, a computer may be used to control excitation of the switchable entities and the acquisition of images of the swichable entities. In one set of embodiments, a sample may be excited using light having various wavelengths and/or intensities, and the sequence of the wavelengths of light used to excite the sample may be correlated, using a computer, to the images acquired of the sample containing the switchable entities. For instance, the computer may apply light having various wavelengths and/or intensities to a sample to yield different average numbers of activated switchable elements in each region of interest (e.g., one activated entity per location, two activated entities per location, etc). In some cases, this information may be used to construct an image of the switchable entities, in some cases at sub-diffraction resolutions, as noted above.

In other aspects of the invention, the systems and methods described herein may also be combined with other imaging techniques known to those of ordinary skill in the art, such as high-resolution fluorescence in situ hybridization (FISH) or immunofluorescence imaging, live cell imaging, confocal imaging, epi-fluorescence imaging, total internal reflection fluorescence imaging, etc.

The following are incorporated herein by reference: U.S. Provisional Patent Application Ser. No. 60/836,167, filed Aug. 7, 2006, entitled "Sub-Diffraction Image Resolution"; and U.S. Provisional Patent Application Ser. No. 60/836,170, filed Aug. 8, 2006, entitled "Sub-Diffraction Image Resolution."

The following examples are intended to illustrate certain embodiments of the present invention, but do not exemplify the full scope of the invention.

EXAMPLE

This example shows a high-resolution optical microscopy, stochastic optical reconstruction microscopy ("STORM"), in which a fluorescence image is constructed from high-accuracy localization of individual fluorescent entities ("fluorophores") that are switched on and off using light of different colors, in accordance with one embodiment of the invention. The STORM imaging process in this example includes a series of imaging cycles (FIG. 1a). In each cycle, a fraction of the fluorophores in the field of view are switched on or activated, such that each of the active fluorophores is optically resolvable from the rest, i.e. their images are not overlapping. This allows the position of these fluorophores to be determined with high accuracy. Repeating this process for multiple cycles, each causing a stochastically different subset of fluorophores to be turned on or activated, enables the positions of many fluorophores to be determined and thus an overall image to be reconstructed. In these examples, an imaging resolution of approximately 20 nm is demonstrated, an improvement of 10 times over the resolution of conventional fluorescence microscopy, using a simple total-internal-reflection fluorescence microscope, low-power continuous-wave lasers, and a photoswitchable cyanine dye.

FIG. 1a shows that a STORM imaging sequence using a hypothetical hexameric object labeled with fluorophores can be switched between a fluorescent (white) and a dark state by a red and green laser, respectively. In this non-limiting illustration, all fluorophores were first switched "off" to the dark state ("deactivated") by a strong red laser pulse. In each imaging cycle, a green laser pulse was used to switch on ("activate") only a fraction of the fluorophores to give an optically resolvable set of active fluorophores. Next, under red illumination ("image"), these molecules emitted fluorescence until they were switched off, allowing their positions (indicated by white crosses) to be determined with relatively high accuracy. The overall image was then reconstructed from the fluorophore positions obtained from multiple imaging cycles.

Figure 1B:
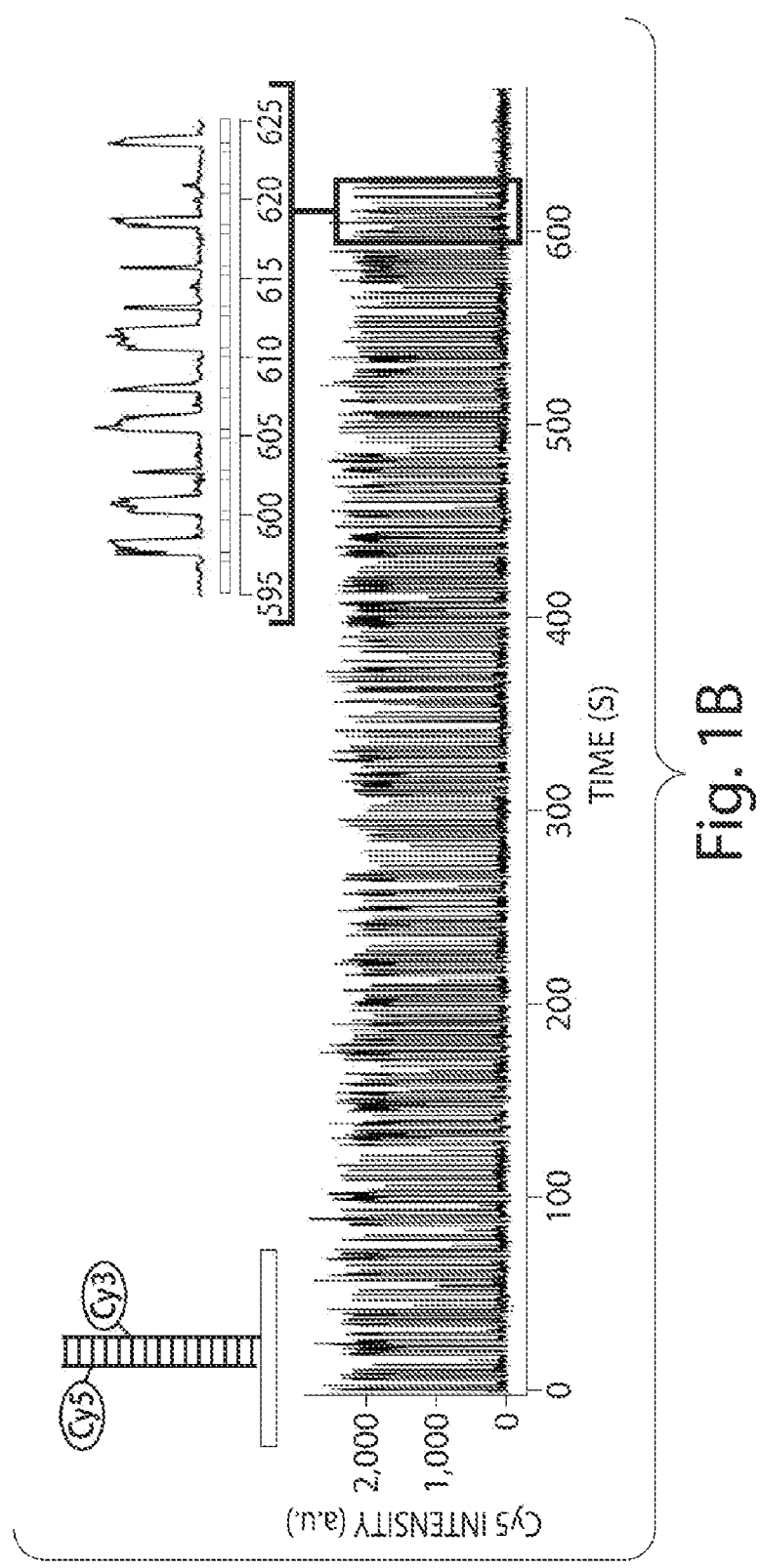
Figure 4:
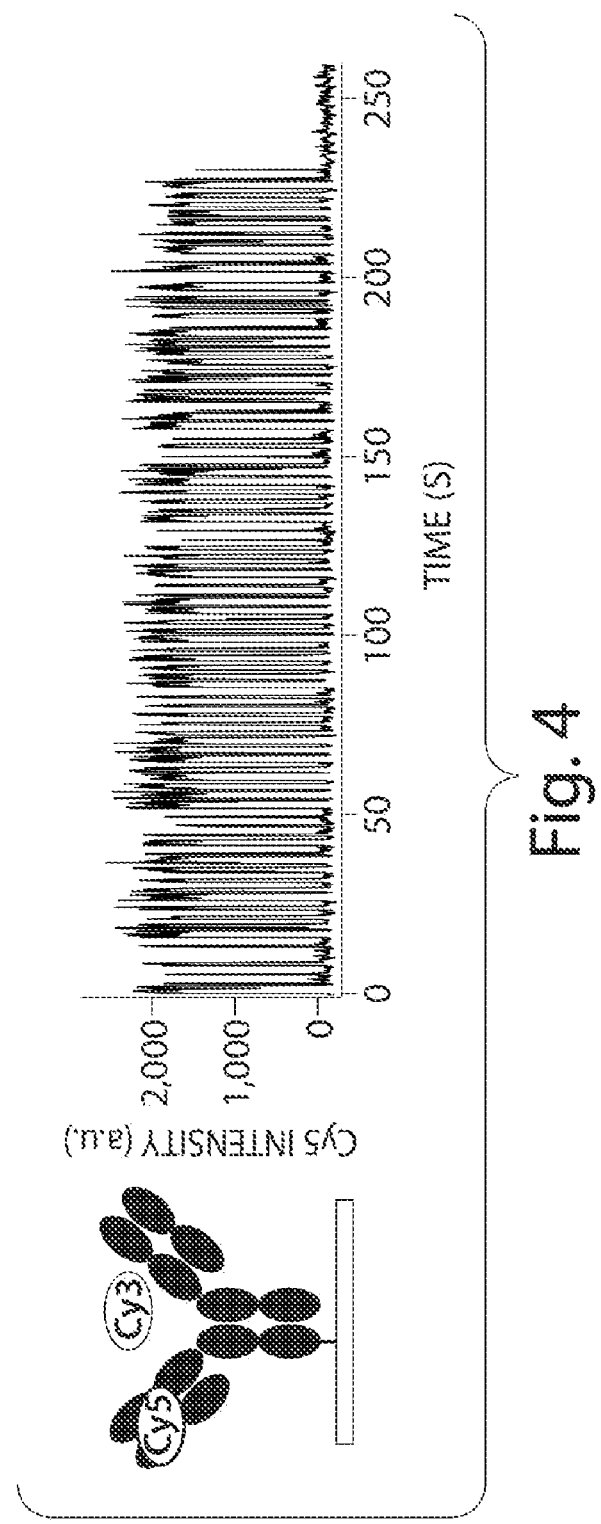
FIG. 4 illustrates the repeated switching of Cy3-Cy5-labeled antibody, in accordance with one embodiment of the invention.

Cyanine dye, Cy5, can be switched between a fluorescent and a dark state in a controlled and reversible manner by light of different wavelengths. Red laser light that produces fluorescent emission from Cy5 can also switch the dye to a stable dark state. Exposure to green laser light converts Cy5 back to the fluorescent state, but the recovery rate may depend in some cases on the close proximity of a secondary dye, Cy3. The Cy3-Cy5 dye pair can also be referred to as a switch. Under illumination conditions allowing single-molecule detection, it was found that such a switch, when attached or immobilized to nucleic acids or proteins, can be cycled on and off hundreds of times before permanent photobleaching occurs (FIG. 1b and FIG. 4). In FIG. 1b, a red laser (633 nm, 30 W/cm$^2$) was used to excite fluorescence (black line) from Cy5 and to switch Cy5 to the dark state. A green laser (532 nm, 1 W/cm$^2$) was used to return Cy5 to the fluorescent state. The alternating red and green line indicates the laser excitation pattern. In some cases, the recovery rate of Cy5 appeared to depend on the close proximity of Cy3.

FIG. 4 shows goat anti-mouse secondary antibody labeled with the cyanine switch exhibits photoswitching behavior similar to switch-labeled DNA. The antibody was labeled with Cy3 and Cy5 (see below) and bound to a quartz slide coated with unlabeled mouse anti-transferrin primary antibody. The trace shows the Cy5 fluorescence intensity detected from a single labeled antibody as it switched on and off until permanent photobleaching occurs after about 230 seconds. The sample was excited with a sequence of alternating green and red laser pulses (0.5 s green followed by 2 s red).

Figure 2A:
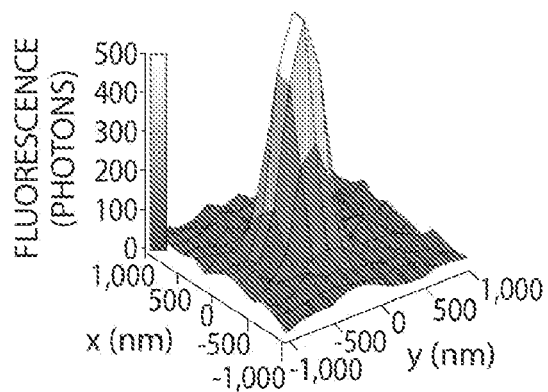
FIGS. 2a-2d illustrate the localization of molecular entities according to another embodiment of the invention.
Figure 2B:
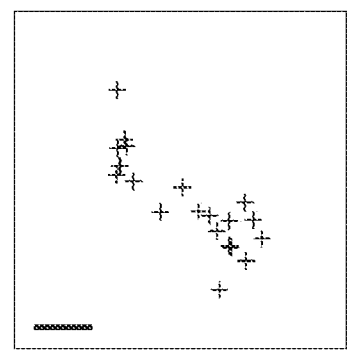
Figure 2C:
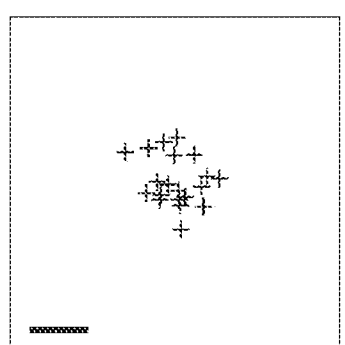
Figure 2D:
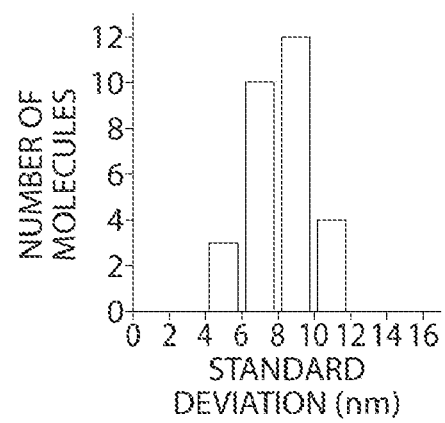

In this example, the concept of STORM is shown using the cyanine switch, but any suitably optically switched fluorophores could also be used. The resolution of STORM may be limited in some cases by the accuracy with which individual switches can be localized during a switching cycle. As an example of determining the localization accuracy, a switch was attached or immobilized to a short double-stranded DNA, which was surface-immobilized at low density so that single switches were resolvable. These switches were periodically cycled on and off using green and red laser light, and the red laser also served to excite fluorescence from Cy5. No fluorescence from Cy3 was recorded in this process. The high localization accuracy of individual switches during each switching cycle defining the intrinsic resolution of STORM is shown in FIG. 2. The fluorescence image from a single switch gave a point-spread function shown in FIG. 2a. The point spread function (PSF) of the emission from a single switch on DNA during a single switching cycle. A Gaussian fit to this image (not shown) was used to localize the centroid position of the PSF, indicating the position of the switch. The positions determined from multiple switching cycles showed a substantial spread (FIG. 2b), which was significantly reduced by correcting for sample drift over the course of the experiment (FIG. 2c, see below for additional details). FIGS. 2b and 2c show the centroid positions of an individual switch determined in 20 successive imaging cycles before (FIG. 2b) and after (FIG. 2c) correction for sample drift. The scale bars are 20 nm. The standard deviation of the drift-corrected positions obtained from 20 imaging cycles was on average 8 nm for individual switches (FIG. 2d). FIG. 2d shows a histogram of the standard deviation of centroid positions. The standard deviation is determined as $(\sigma_x+\sigma_y)/2$ ((sigma-x+sigma-y)/2) for each switch using 20 imaging cycles, where $\sigma_x$ (sigma-x) and $\sigma_y$ (sigma-y) are the standard deviations of the centroid positions in the x and y dimensions. This histogram was constructed from 29 switches. This value gave a measure of the uncertainty in the localization of a single switch per imaging cycle. Correspondingly, the experimentally measured spread of switch positions follows a Gaussian distribution with a FWHM of 18 nm, as expected from the 8 nm standard deviation (FIG. 5). Therefore, under these imaging conditions, two switches separated by 20 nm could be resolved.

Figure 5A:
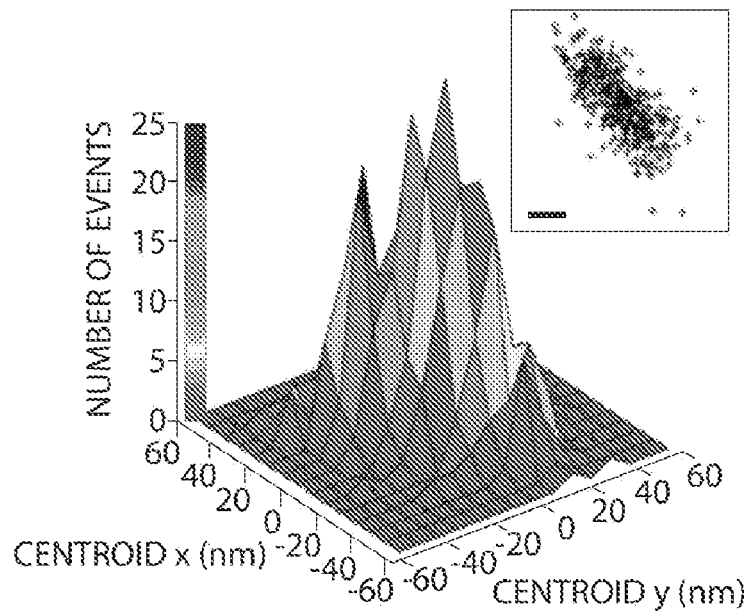
FIGS. 5a-5b illustrate drift correction in another embodiment of the invention.
Figure 5B:
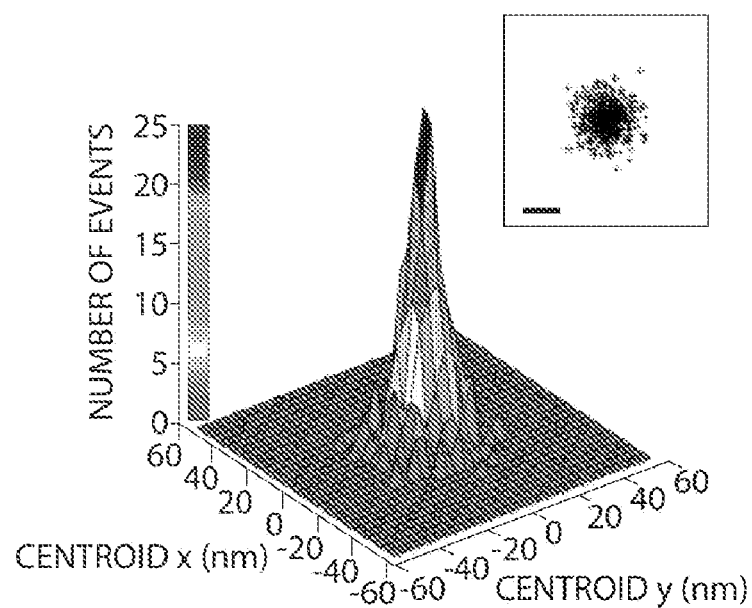

FIG. 5 shows the superimposed position distributions of 29 individual switches before (FIG. 5a) and after (FIG. 5b) correction for stage drift. The scale bar is 20 nm. To obtain these distributions, the image of each switch during a given imaging cycle was fit to a two-dimensional Gaussian function, yielding the centroid position of each switch during that cycle. Twenty imaging cycles were carried out, giving twenty measured positions per switch. The position data for each switch were realigned so that the average position of each switch was at the origin, and the measurements from different switches were then superimposed to give the overall position distribution shown in the insets. The main plots are histograms of these centroid positions. The uncorrected distribution is fairly broad and skewed asymmetrically. After correction for stage drift using fiducial markers (see below) the distribution become significantly narrower. The fit of the drift-corrected histogram to a Gaussian gave a full width at half-maximum of 18±2 nm.

Figure 3A:
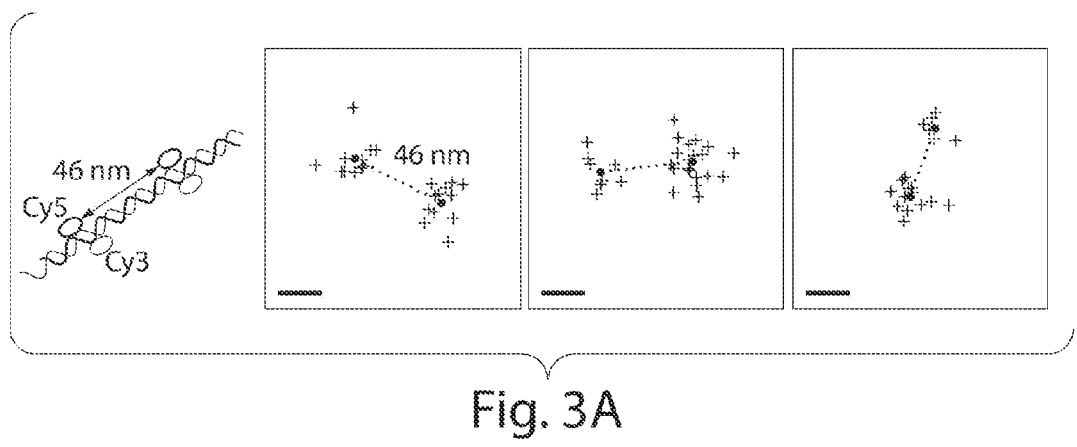
FIGS. 3a-3d illustrate the sub-diffraction localization of molecular entities according to yet another embodiment of the invention.
Figure 3B:
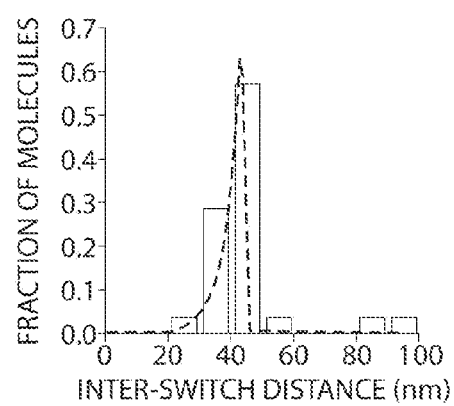
Figure 3C:
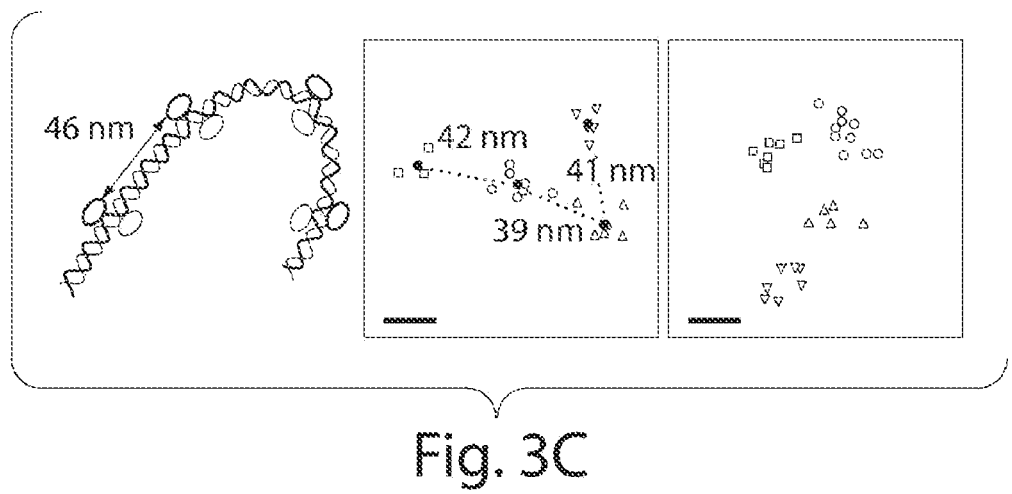

To demonstrate the capability of STORM to resolve fluorescent molecules in close proximity, standard samples of linear, double-stranded DNA labeled were constructed with multiple switches separated by a well-defined number of base pairs (see methods, below, for details). The DNA strands were also labeled with multiple biotins and attached to a high-density streptavidin layer (see below), increasing the likelihood of multiple attachments between the DNA and the surface so that the DNA was immobilized in the plane. DNA strands were first examined containing two switches separated by 135 base-pairs (FIG. 3a and FIG. 6), corresponding to a length of 46 nm along the DNA contour. A STORM image obtained using the imaging procedure described above (see below for details) showed two clusters of measured switch positions, indicating that the two switches were well-resolved (FIG. 3a). This image shows two separated clusters of measured switch positions (crosses), each corresponding to a single switch. The center-of-mass position of each cluster is marked by a dot. The inter-switch distances are 46 nm, 44 nm and 34 nm for these three examples. The scale bars are 20 nm. The distance between the centers of the two clouds had a mean value of 41 nm (FIG. 3b), in quantitative agreement with the theoretical mean (40 nm) determined using the known contour and persistence lengths of the DNA sample (see below). FIG. 3b shows a comparison between the inter-switch distances measured using STORM (grey column) and the predicted distance distribution considering the flexibility of DNA (dashed line). FIG. 3c shows STORM images of four switches attached to a double-stranded DNA, pair-wise separated by a contour length of 46 nm. The measured switch positions were clustered by an automated algorithm (see below for details) and different clusters are indicated by different symbols. The scale bars are 20 nm.

Figure 6:
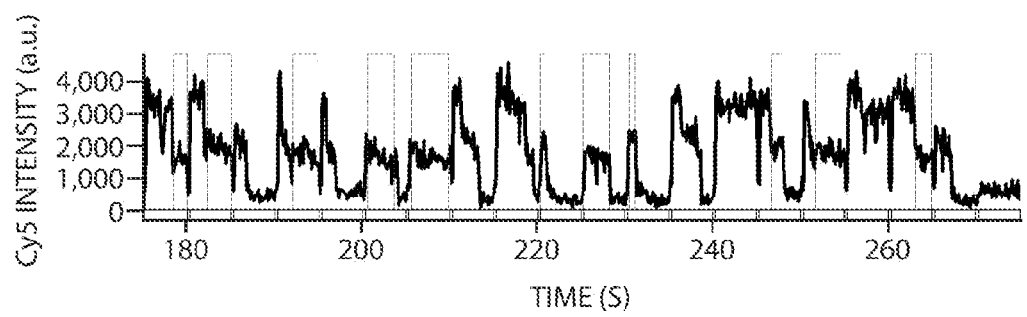
FIG. 6 illustrates the repeated switching of a molecular switch, in yet another embodiment of the invention.

FIG. 6 is an excerpt of a fluorescence trace (black line) showing the cycling of Cy3-Cy5 switches separated by a contour length of 46 nm on dsDNA (see also FIG. 3a). Each switching cycle lasted for 5 seconds and included a brief green pulse (underlying tick marks) to activate one or two switches followed by a long red exposure (underlying bar) to excite Cy5 fluorescence and return the switches to the off state. In cycles when one switch is activated (e.g. 225-230 seconds), a single intensity level was apparent before the return to the dark state. In cycles where two switches are activated (e.g. 245-250 seconds), a "staircase" with two decreasing levels corresponding to the sequential switching off of each dye is observed. Regions where only a single switch is on and all of the peak quality criteria are satisfied (see below) were used for single-switch localization.

Longer DNA samples labeled with four switches evenly separated by 46 nm along the contour were also imaged. The STORM images revealed four clusters of switch positions following a bent contour consistent with the persistence length of DNA and the engineered separation between the switches. These results indicated that STORM can image biological samples with sub-diffraction-limit resolution and that features separated by 40 nm are well within the resolving power.

Figure 3D:
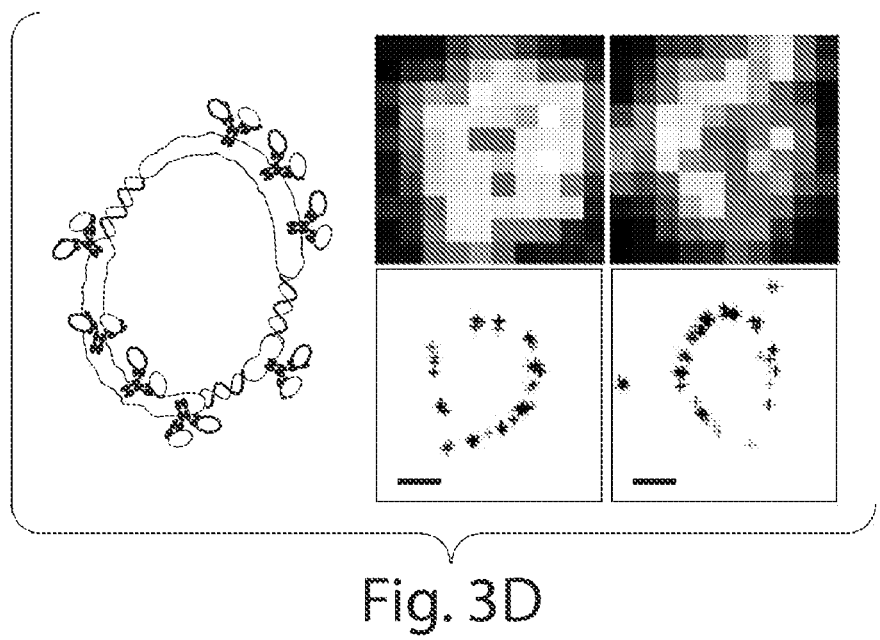

One advantage of STORM is its ability to localize a large number of switches within a diffraction-limited spot by cycling the switches on and off in a controlled manner, allowing this to be used as a general biological imaging technique. To demonstrate this capability, circular DNA plasmids were prepared and coated with RecA protein and imaged using indirect immunofluorescence with switch-labeled secondary antibody (FIG. 3d, see methods, below, for details). STORM images of the RecA filaments revealed their circular structure with greatly increased resolution when compared with wide-field images. Parts of the filament appear to be unlabeled or kinked, which may correspond to regions of the plasmid that remain uncoated by RecA. In FIG. 3d, the top panels show indirect immunofluorescence images with switch-labeled secondary antibody taken by a total internal reflection microscope. The bottom panels are the reconstructed STORM images of the same filaments. The scale bars are 300 nm.

In summary, this example demonstrates that STORM is capable of imaging biological structures with sub-diffraction limit resolution. The resolution of the technique is not the wavelength of light. For the cyanine switch, approximately 3,000 photons were detected per switching cycle, independent of red laser intensity (data not shown), predicting a theoretical localization accuracy of 4 nm. The difference between this theoretical prediction and the measured accuracy of 8 nm is relatively small, and the discrepancy may be due to imperfect correction of stage drift and aberration due to focus drift in the measurements. This measured localization accuracy corresponds to an imaging resolution of approximately 20 nm. Indeed, fluorescent switches separated by 40 nm were readily resolved (FIG. 3).

The cyanine switches could be turned on and off reliably for hundreds of cycles before photobleaching, allowing STORM to be used for resolving structures with many fluorophores in a potentially time-resolved manner. The circular structure of RecA filaments containing 10-20 switches could be resolved in a few minutes. The imaging speed may be improved by increasing the switching rate through stronger excitation or fluorophores with faster switching kinetics. STORM is thus a valuable tool for applications such as high-resolution fluorescence in situ hybridization (FISH) or immunofluorescence imaging. The STORM concept is also applicable to other photo-switchable fluorophores and fluorescent proteins, which will potentially allow high-resolution live-cell imaging with endogenous labels, and any other imaging applications in which sub-diffraction image resolution is desired.

Following are methods useful in the above description.

Preparation of switch-labeled DNA constructs. Biotinylated and/or amine-modified DNA oligonucleotides ("oligos") were purchased, PAGE purified, from Operon. Amine-modified oligos were labeled with amine reactive Cy3 or Cy5 (Amersham Bioscience) post-synthetically following the protocol provided by the manufacturer. The dye-labeled oligos were purified using reverse phase HPLC. Complementary strands of DNA were annealed to form biotinylated double-stranded DNA (dsDNA) by mixing equimolar amounts of the two complementary strands in 10 mM Tris-Cl (pH 7.5), 50 mM NaCl, heating to 90° C. for two minutes, and then allowing the mixture to cool to room temperature in a heat block over a period of one hour.

Biotinylated dsDNA of varying lengths having an intra-switch distance of 135 bp were constructed by annealing complimentary oligos as described above to form three different 45 bp dsDNA segments denoted A, B, and C, followed by a ligation reaction. The oligos were designed with specific sticky ends which only permit A to ligate to B, B to ligate to C and C to ligate to A, reading in the 5' to 3' direction. One oligo (A) contained amine-reactive sites three base pairs apart on opposite strands which were specifically labeled with Cy3 and Cy5 prior to annealing to form the optical switch. Oligos B and C contain two internal biotin modifications per strand to facilitate multivalent linkage to the streptavidin surface. After annealing, the oligos were mixed at equal concentrations and ligated overnight using T4 ligase (New England Biolabs). The resulting ligation product was purified on a 1.5% agarose gel to select bands containing the desired concatamerized dsDNA length.

Preparation of switch-labeled antibodies. Goat polyclonal to mouse IgG secondary antibodies (Abcam ab6708) were labeled non-specifically with amine-reactive Cy3 and Cy5. The average dye-to-antibody ratio was characterized to be 2.2:1 for Cy3 and 0.1:1 for Cy5 using a UV-Vis spectrometer. These labeling ratios were chosen to minimize the fraction of antibodies labeled with more than one Cy5 molecule, due to the inefficient switching observed for antibodies labeled with multiple Cy5. The presence of more than one Cy3 molecule on a single antibody did not interfere with switching. With this labeling ratio, a large fraction of the secondary antibody did not carry Cy5, and were not observed. This lower density of labels is typically not a problem for indirect immunofluorescence imaging and, in particular, did not prevent resolution of the circular structure of the RecA-plasmid filaments.

Preparation of RecA filaments. Biotinylated RecA was prepared by reacting purified recombinant RecA (New England Biolabs) with amine-reactive biotin-XX (Invitrogen) in 0.1 M carbonate buffer at pH 8.3. The resulting biotinylated protein was purified on a NAP-5 size exclusion column (Amersham). RecA filaments were formed on ΦXRF-II (Phi-XRF) plasmid DNA (New England Biolabs) by incubating RecA (25% biotinylated: 75% unbiotinylated, concentration of 80 micrograms/mL) with plasmid DNA (2 micrograms/mL) in 10 mM Tris buffer at pH 7.0, 100 mM NaCl, 7 mM $MgCl_2$, and 0.8 mg/mL ATP-γ-S (ATP-gamma-S) for 1 hour at 37° C. The resulting RecA-DNA filaments were stored at 4° C. and used for imaging the same day.

Microscope slide preparation. Quartz microscope slides (G. Finkenbeiner) were cleaned using Alconox detergent, followed by sonication for 15 minutes in acetone, 1 M aqueous KOH, ethanol, 1 M aqueous KOH, sequentially. Slides being prepared for lipid bilayers were submerged into a 5% HF solution for 2 hours after the second KOH step. Finally, the slides were rinsed with deionized water, and flame dried. The flow channels were prepared using two pieces of double-sided adhesive tape (3M) and covered with a No. 1.5 glass coverslip (VWR).

Oxygen scavenging system. All imaging buffers were supplemented with the oxygen scavenging system, which included 10% (w/v) glucose (Sigma), 0.1% (v/v) beta-mercaptoethanol (Sigma), 500 micrograms/mL glucose oxidase (Sigma), and 10 micrograms/mL catalase (Roche). The oxygen scavenging system was important for reliable photo-switching of the fluorophores.

Surface-immobilization of DNA and antibodies. To immobilize the DNA sample labeled with multiple switches on a quartz slide, a lipid bilayer was first formed on the slide by flowing in liposomes of egg PC and 5% biotin-PE (Avanti). The liposomes were formed according to the manufacturer's instructions, extruded through a 0.05 micrometer filter membrane at a concentration of 5 mg lipids/mL in DI water, and then mixed with a 1:1 ratio with a buffer containing 10 mM Tris at pH 8.0, 100 mM NaCl immediately before use. After a 2 hour incubation the bilayer was rinsed extensively with 50 mM Tris at pH 8.0, 10 mM NaCl, and the bilayer was incubated with streptavidin (0.25 mg/mL, Invitrogen) for 30 minutes. After extensive washing, the streptavidin surface was crosslinked in 4% v/v formaldehyde in PBS for 1 hour and rinsed with Tris buffer before allowing the biotinylated, switch-labeled DNA to bind. DNA was imaged in Tris buffer (50 mM Tris-Cl at pH 7.5, 10 mM NaCl) with the oxygen scavenging system described above.

To immobilized switch-labeled antibodies on a surface, the quartz slides were cleaned as described and incubated for 5 minutes with mouse anti-transferrin IgG (Abcam) allowing it to bind non-specifically. The slide was then incubated with the labeled secondary antibodies in PBS buffer containing 3% bovine serum albumin (BSA) for 10 min. The buffer was replaced with 50 mM Tris, 10 mM NaCl, pH 7.5 containing the oxygen scavenging system for imaging.

Immunofluorescence imaging of RecA-dsDNA filaments. Biotinylated RecA-dsDNA filaments were attached via streptavidin linkages to a quartz slide non-specifically coated with biotinylated BSA. The surface was then washed with 50 mM Tris at pH 7.0, 100 mM NaCl, 7 mM $MgCl_2$, 3% BSA w/v (block buffer) and incubated for 30 minutes to block the surface against non-specific antibody binding. The slide was then incubated in this block buffer containing monoclonal mouse antibody against RecA (Stressgen) at 2 microgram/mL for 1 hour. After extensive washing with block buffer, the slide was incubated in the block buffer containing switch-labeled secondary antibody at 0.3 microgram/mL for 1 hour. Finally, the sample was washed and imaged in 50 mM Tris at pH 7.5, 100 mM NaCl, 7 mM $MgCl_2$, supplemented with the oxygen scavenging system as described above.

Imaging procedures. An Olympus IX71 microscope was used for single-molecule imaging with the prism-type total internal-reflection excitation scheme. The samples were excited with a 633 nm HeNe laser (Melles Griot) and a 532 nm diode-pumped Nd:YAG laser (Crystalaser). The fluorescence emission of Cy5 was collected with a N.A. 1.25 60× water immersion objective, and imaged onto an electron multiplying CCD camera (Andor Ixon DV897) after passing through a 665 nm long pass filter (Chroma). The images were recorded at a frame rate of 9.7 Hz. To track motion of the sample stage, 200 nm red fluorescent polystyrene beads (Invitrogen, F-8810) were added to the slide in Tris buffer containing 10 mM $MgCl_2$ and allowed to bind to the surface. Data was acquired using custom data acquisition software written in Labview, which enabled sequences of alternating red and green laser excitation pulses to be applied to the sample, switching the dyes on and off. Laser excitation was synchronized with the camera exposure to 1 ms accuracy.

Imaging experiments on DNA concatamers typically included of 60 laser pulse cycles to activate and deactivate the switches, where each cycle lasted for 5 s, so that the final image took 5 minutes to acquire. The multiple cluster configuration of the centroid position distribution is typically apparent within 2 minutes. The experiments on antibody-labeled RecA-dsDNA filaments included 70 switch cycles, each lasting 10 s. The ring shape of the RecA-dsDNA filaments typically became evident within 2 minutes, although the position of every switch present in the sample had not yet been identified by this time. As the rate of switching depended linearly on the excitation intensity, the cycling time, and hence the overall imaging time, could be shortened without substantially affecting the localization accuracy by increasing the red laser intensity. The green laser intensity was chosen so that typically 1-3 switches were switched on during the green pulse and, in most cases, all activated switched were turned off during the red phase of the cycle.

Raw images of RecA-dsDNA for comparison with STORM reconstructed images were formed by taking the maximum fluorescence value recorded for each pixel throughout the imaging sequence so that each switch would be equally represented regardless of the amount of time it spent in the fluorescent or dark states.

Image analysis. Fluorescent structures (DNA or RecA filaments) in an averaged image were first isolated in 13×13 pixel square fitting window for data analysis. In a given window, the total fluorescence intensity was integrated in each frame to produce a fluorescence time trace (see FIG. 6). Several criteria were used to ensure high accuracy localization of single switches:

(1) In each switching cycle, only regions where a single switch is on for at least three frames (0.3 seconds) were used for localization analysis (see FIG. 6).

(2) The fluorescence images within these regions were fit by nonlinear least-squares regression to a continuous ellipsoidal Gaussian:

$$I(x,y) = A + I_0 e^{[-(x'/a)^2 - (y'/b)^2]/2}$$

where:

$$x' = (x-x_0)\cos\theta - (y-y_0)\sin\theta$$

$$y' = (x-x_0)\sin\theta + (y-y_0)\cos\theta$$

Here, A is the background fluorescence level, $I_0$ is the amplitude of the peak, a and b reflects the widths of the Gaussian distribution along the x and y directions, $x_0$ and $y_0$ describe the center coordinates of the peak, and θ (theta) is the tilt angle of the ellipse relative to the pixel edges. Based on this fit, the peak ellipticity defined as $|2(a-b)/(a+b)|$ was computed. If this ellipticity exceeded 15%, indicating poor image quality or the possible presence of multiple active switches, the region was rejected from the analysis.

(3) The total number of counts collected in the peak was calculated as $2\pi$ ab $I_0$ (2 pi ab $I_0$) and then converted to photoelectrons, and thus the number of photons detected, using the camera manufacturer's calibrated curve for the electron multiplication and ADC gain settings used during imaging. If the total number of photoelectrons in the peak was less than 2,000, the region was rejected due to insufficient statistics to achieve high localization accuracy.

The regions of the fluorescence traces that passed the above tests were used for the final localization analysis. The fluorescence images corresponding to these regions were subjected to a final fit using a pixelated Gaussian function to determine the centroid position. Because the CCD chip included square pixels of finite size, for optimum accuracy, the image was fit to:

$$I(x,y) = A + \int_{x-\delta}^{x+\delta} dX \int_{y-\delta}^{y+\delta} dY\, I_0 e^{\left[-\left(\frac{X-x_0}{a}\right)^2 - \left(\frac{Y-y_0}{b}\right)^2\right]/2}$$

which, for ease of evaluation, can be re-expressed in terms of error functions as:

$$I(x,y) = A + I_0 \frac{ab\pi}{4}\left[\mathrm{erf}\left(\frac{x+\delta-x_0}{a}\right) - \mathrm{erf}\left(\frac{x-\delta-x_0}{a}\right)\right]$$
$$\left[\mathrm{erf}\left(\frac{y+\delta-y_0}{b}\right) - \mathrm{erf}\left(\frac{y-\delta-y_0}{b}\right)\right]$$

where A, $I_0$, a, b, $x_0$ and $y_0$ are as defined previously and δ (delta) is the fixed half-width of a pixel in the object plane. The final centroid coordinates ($x_0$, $y_0$) obtained from this fit were used as one data point in the final STORM image.

To correct for mechanical drift in the microscope during imaging, the same fitting algorithm was used to automatically track the motion of several fluorescent beads in the field of view. The beads served as fiducial marks and their positions were sampled during each imaging cycle. The averaged motion of the beads was subtracted from the coordinates obtained for each single switch position, yielding a drift-corrected reconstructed image.

For quantitative analysis of images using switches equally spaced on dsDNA, the coordinates in the reconstructed image were classified using a k-means clustering algorithm, and inter-switch distances were calculated as the distance between the cluster centroids. The number of clusters input to the algorithm was chosen according to the number of photobleaching steps observed during the initial exposure to red light.

Prediction of DNA configuration. Possible configurations of a 135 bp piece of dsDNA bound to the surface were computed by Monte Carlo simulation of the DNA as a worm-like chain in the plane. According to the Watson-Crick structure of dsDNA and accounting the length of the $C_6$ linkers attaching the Cy5 molecules to the nucleotides, the expected contour length between neighboring Cy5 molecules of 46±1 nm was calculated. The DNA was treated as a series of 1 Å (Angstrom) joints lying in the plane, each of which was deflected by a random angle selected from a Gaussian distribution chosen to give a persistence length of 50 nm. The measured inter-switch spacing was compared to the distribution of end-to-end distances of the polymer in this simulation.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of imaging a sample comprising photoswitchable fluorescent probes, the method comprising:
   (a) providing a sample labeled with a plurality of photoswitchable fluorescent probes, at least some of the photoswitchable fluorescent probes being separated by a distance of less than about 1000 nm, at least some of the photoswitchable fluorescent probes being in a state not capable of emitting light at a first wavelength;
   (b) exposing the plurality of photoswitchable fluorescent probes to substantially identical activation light to activate a statistical subset of the photoswitchable fluorescent probes from a state not capable of emitting light at the first wavelength to a state capable of emitting light at the first wavelength;
   (c) exciting the activated subset of photoswitchable fluorescent probes with excitation light to cause the activated subset to emit light at the first wavelength;

(d) determining light emitted at the first wavelength by the activated subset of photoswitchable fluorescent probes;

(e) substantially deactivating the activated subset of photoswitchable fluorescent probes;

(f) repeating (b) through (e) one or more times, each time activating a statistically different subset of the plurality of photoswitchable fluorescent probes; and (g) determining the positions of at least some of the photoswitchable fluorescent probes within the sample by using the light emitted by the activated subsets of the photoswitchable fluorescent probes.

2. The method of claim 1, wherein the act of determining light emitted by the activated subsets of photoswitchable probes comprises acquiring an image of the light emitted by the activated subsets of the photoswitchable fluorescent probes.

3. The method of claim 1, wherein the act of determining the positions of at least some of the photoswitchable fluorescent probes comprises using Gaussian fitting of the light emitted by the activated subsets of the photoswitchable fluorescent probes.

4. The method of claim 1, wherein the positions of at least some of the photoswitchable fluorescent probes are determined to a precision that is smaller than the first wavelength.

5. The method of claim 4, wherein the precision defined by the full width at half maximum (FWHM) is smaller than about 20 nm.

6. The method of claim 1, wherein the act of determining the positions of at least some of the photoswitchable fluorescent probes comprises using drift correction to determine the positions of at least some of the photoswitchable fluorescent probes.

7. The method of claim 6, wherein the act of using drift correction comprises using fiduciary markers to determine drift.

8. The method of claim 1, comprising determining the positions of at least some of the photoswitchable fluorescent probes as a function of time.

9. The method of claim 1, wherein at least some of the photoswitchable fluorescent probes comprises a first, light-emitting portion and a second, activation portion that activates the first portion upon exposure to light.

10. The method of claim 9, wherein the first portion is Cy5, Cy5.5, or Cy7 and the second portion is Cy2, Alexa Fluor 488, Cy3, Cy3.5, or Cy5.

11. The method of claim 1, wherein the activation light of (b) has an intensity sufficient to activate, on average, a statistical subset but not all of the photoswitchable fluorescent probes that the activation light is incident thereto.

12. The method of claim 1, wherein (e) comprises substantially deactivating the activated subset of photoswitchable fluorescent probes by exposing at least the activated subset of photoswitchable fluorescent probes to deactivation light.

13. The method of claim 1, wherein substantially all of the photoswitchable fluorescent probes are essentially identical.

14. The method of claim 1, wherein (a) comprises:
providing a sample labeled with a plurality of photoswitchable fluorescent probes; and
deactivating at least some of the photoswitchable fluorescent probes by exposing the photoswitchable fluorescent probes to deactivation light such that at least some of the photoswitchable fluorescent probes are placed in a state not capable of emitting light at a first wavelength.

15. The method of claim 1, wherein (g) comprises determining the positions of at least some of the photoswitchable fluorescent probes within the sample to a precision of less than about 300 nm.

16. The method of claim 1, wherein (g) comprises determining the positions of at least some of the photoswitchable fluorescent probes within the sample to a precision of less than about 100 nm.

17. The method of claim 1, wherein (g) comprises determining the positions of at least some of the photoswitchable fluorescent probes within the sample to a precision of less than about 40 nm.

18. The method of claim 1, wherein (g) comprises determining the positions of at least some of the photo switchable fluorescent probes within the sample to a precision of less than about 20 nm.

* * * * *